United States Patent
Saks

(10) Patent No.: US 9,802,059 B2
(45) Date of Patent: Oct. 31, 2017

(54) OPHTHALMOLOGICAL DEVICE AND METHOD FOR THE TREATMENT OF CORNEAL DISEASES

(76) Inventor: Asher Abraham Saks, Cape Town (ZA)

( * ) Notice: Subject to any disclaimer, the term of this patent is extended or adjusted under 35 U.S.C. 154(b) by 0 days.

(21) Appl. No.: 14/002,756

(22) PCT Filed: Feb. 14, 2012

(86) PCT No.: PCT/IB2012/050649
§ 371 (c)(1),
(2), (4) Date: Sep. 3, 2013

(87) PCT Pub. No.: WO2012/127330
PCT Pub. Date: Sep. 27, 2012

(65) Prior Publication Data
US 2014/0039377 A1    Feb. 6, 2014

(30) Foreign Application Priority Data
Mar. 23, 2011 (ZA) .................. 2011/02174

(51) Int. Cl.
| | | |
|---|---|---|
| A61N 5/06 | (2006.01) | |
| A61B 17/30 | (2006.01) | |
| A61F 9/007 | (2006.01) | |
| A61F 9/008 | (2006.01) | |

(52) U.S. Cl.
CPC .......... *A61N 5/0613* (2013.01); *A61F 9/0079* (2013.01); *A61N 5/062* (2013.01); *A61B 2017/306* (2013.01); *A61F 9/00781* (2013.01); *A61F 2009/00853* (2013.01); *A61N 2005/0661* (2013.01)

(58) Field of Classification Search
CPC .... A61F 9/009; A61F 9/0079; A61F 9/00781; A61F 2009/00853; A61N 5/0613; A61N 5/062; A61N 2005/0661; A61B 2017/306
See application file for complete search history.

(56) References Cited

U.S. PATENT DOCUMENTS

| | | | |
|---|---|---|---|
| 2006/0161144 A1* | 7/2006 | Li | ................................... 606/10 |
| 2010/0114109 A1* | 5/2010 | Peyman | ....................... 606/107 |

FOREIGN PATENT DOCUMENTS

| | | |
|---|---|---|
| EP | 0627207 | 12/1994 |
| EP | 1561440 | 8/2005 |
| WO | WO0124727 | 4/2001 |

* cited by examiner

*Primary Examiner* — Gary Jackson
*Assistant Examiner* — Scott T Luan
(74) *Attorney, Agent, or Firm* — Skinner and Associates; Joel Skinner

(57) ABSTRACT

An ophthalmological device (10) for the treatment of corneal diseases such as keratocanus and glaucoma, comprises a molding head (12), a suction body (14) and a UV lamp (15). The molding head (12) has a hollow cylindrical configuration and includes a rigid molding lens (18) for shaping the cornea of an eye (11) of a patient. The lens is curved and defines a plurality of apertures therein. The suction body (14) has a hollow cylindrical configuration. The lamp (15) is fitted to the suction body. Molding head (12) and suction body (14) together define a chamber (32) from which air is evacuated so as to induce a partial vacuum within the chamber (32) for attracting the cornea onto the lens (18). A photo-sensitizer is applied to the eye and while the cornea is held against the mold, it is irradiated with UV light by lamp (15) so as to cross-link collagen fibers in the cornea.

7 Claims, 2 Drawing Sheets

OPHTHALMOLOGICAL DEVICE AND METHOD FOR THE TREATMENT OF CORNEAL DISEASES

FIELD OF INVENTION

The invention relates to an ophthalmological device and method for the treatment of corneal diseases such as keratoconus and glaucoma.

BACKGROUND OF THE INVENTION

Various methods for treating corneal diseases such as keratoconus and glaucoma are known.

Keratoconus is a bilateral degenerative disorder of the eye that progressively thins and distorts the cornea, changing it to a more conical shape than its normal curvature. The cornea of the eye becomes thinner with a consequent reduction in rigidity and stability. This typically leads to substantial visual impairment and corneal scarring. In most cases, corrective lenses are effective to allow a patient to function normally. Under the influence of the internal pressure of the eye, weakening of the cornea leads to the eye bulging outward which in turn leads to the eye becoming ametropic. There is considerable risk of the ametropia becoming more severe if the disease is not treated effectively. However, further progression of the disease may require treatments such as the insertion of intrastromal corneal ring segments, corneal collagen cross-linking or corneal transplantation.

It has been found that a cross-linking of the collagen fibres of the cornea may increase the rigidity of the cornea such that the cornea may better resist the internal pressure on the eye. For this purpose, it is known to use a photo-sensitizer such as riboflavin or a riboflavin solution which is applied onto the eye. Such a photo-sensitizer is able, under the influence of photons, to chemically react with the corneal tissue. After the riboflavin has been absorbed by the eye, the eye is exposed to an irradiation with ultraviolet (UV) radiation. Under the influence of the UV radiation, the photo-sensitizer induces a cross-linking of the collagen fibres, thereby increasing the biomechanical rigidity of the cornea such that the cornea is likely to deform less under the influence of the pressure of the eye.

Glaucoma is a disorder of the eye wherein the optic nerve is damaged causing a loss of visual field. Raised intraocular pressure is a risk factor for developing glaucoma. The treatments for glaucoma include the use of medication such as eye drops for reducing intraocular pressure and both laser and conventional surgery.

Any reference herein to a "photo-sensitizer" must be interpreted to mean a reference to a substance which under the influence of photons, is able to chemically react with corneal tissue absorbing the photo-sensitizer so as to cross-link corneal collagen and thereby increase the rigidity of the corneal tissue.

SUMMARY OF INVENTION

According to a first aspect of the invention there is provided an ophthalmological device for the treatment of corneal diseases, which includes:

a mould having a curved, transparent moulding surface defining a plurality of apertures therein, which is applied to the cornea of an eye of a patient for shaping the corneal tissue to a desired curvature;

a suction body defining a suction chamber in which a partial vacuum is induced so as to form a partial vacuum within the mould which attracts the cornea onto the moulding surface; and a radiation source for irradiating the cornea with a beam of radiation.

The mould may include a rigid lens which defines said curved moulding surface, the moulding surface of the lens having a predetermined curvature so as to shape the corneal tissue to said desired curvature. The mould lens may be in the form of a rigid contact lens. The mould may be removably connected to the suction body. In use, this permits the mould to be removed and replaced by another mould with a lens having a different curvature.

The suction body may be in the form of an elongate, hollow tube having a connecting formation at a lower end thereof to which the mould is removably connected.

One of the suction body and the mould may have a connector to which a conduit connected to a suction device such as a suction pump, can be connected, in use.

The radiation source may be in the form of a lamp which is operable to emit a beam of UV light. More specifically, the radiation source may be operable to emit a beam of UV light having a wavelength of 375 nm.

According to a second aspect of the present invention there is provided a method of treating corneal diseases, which includes:

applying an effective amount of a photo-sensitizer to a cornea of an eye of a patient;

applying a mould to the cornea thereby to shape the cornea until a desired corneal shape is achieved;

applying a suction to the cornea so as to attract the cornea onto the moulding surface of the mould; and irradiating the cornea with a focused beam of radiation thereby to induce a cross-linking of collagen fibres in the cornea while the cornea is attracted onto the moulding surface of the moulding.

BRIEF DESCRIPTION OF THE DRAWINGS

Further features of the invention are described hereinafter by way of a non-limiting example of the invention, with reference to and as illustrated in the accompanying diagrammatic drawings. In the drawings:

FIG. 3 shows a bottom plan view of the device of FIG. 1.

DETAILED DESCRIPTION OF THE DRAWINGS

Figure 1:
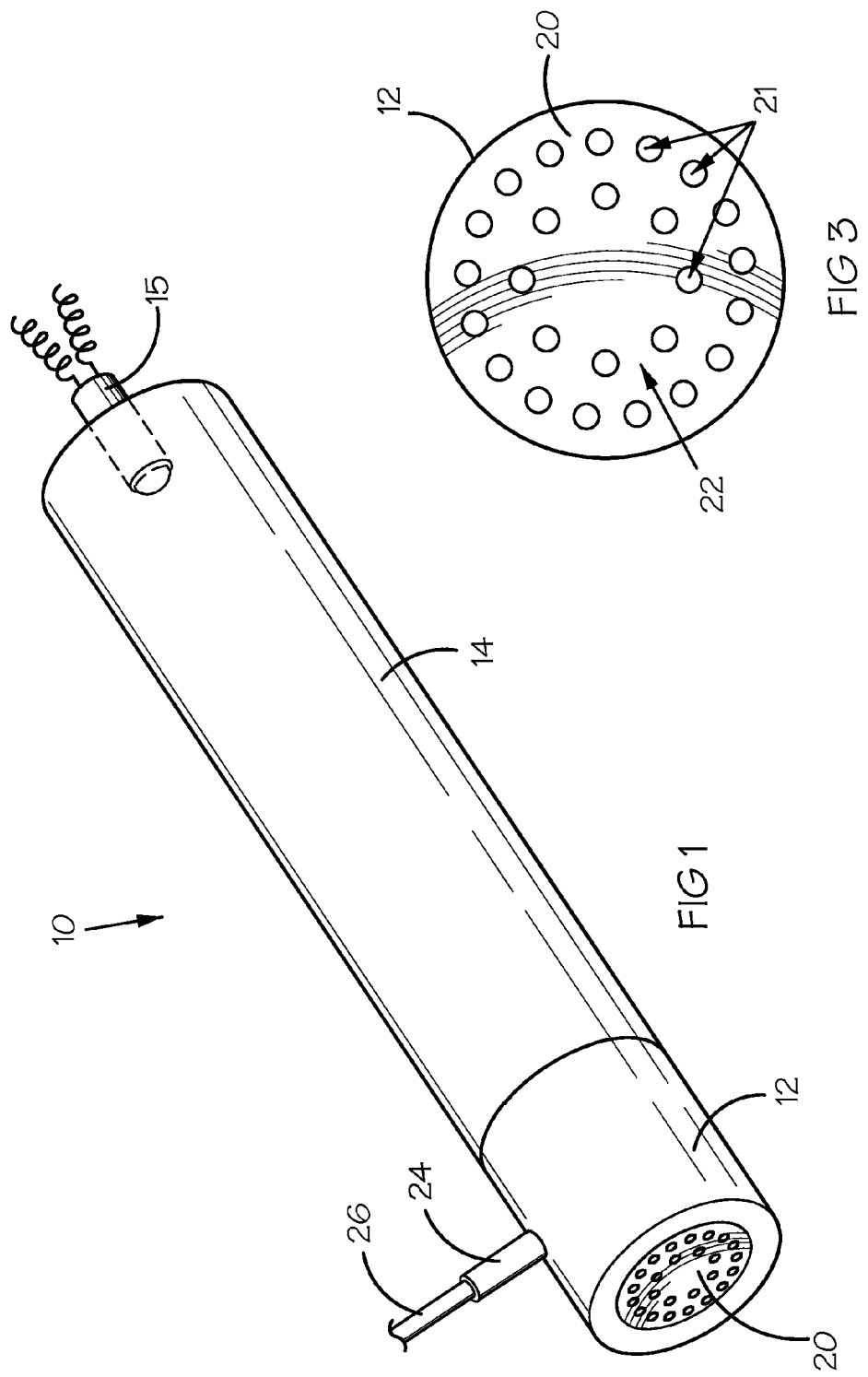
FIG. 1 shows a side view of a device for the treatment of corneal diseases, in accordance with the invention.
Figure 2:
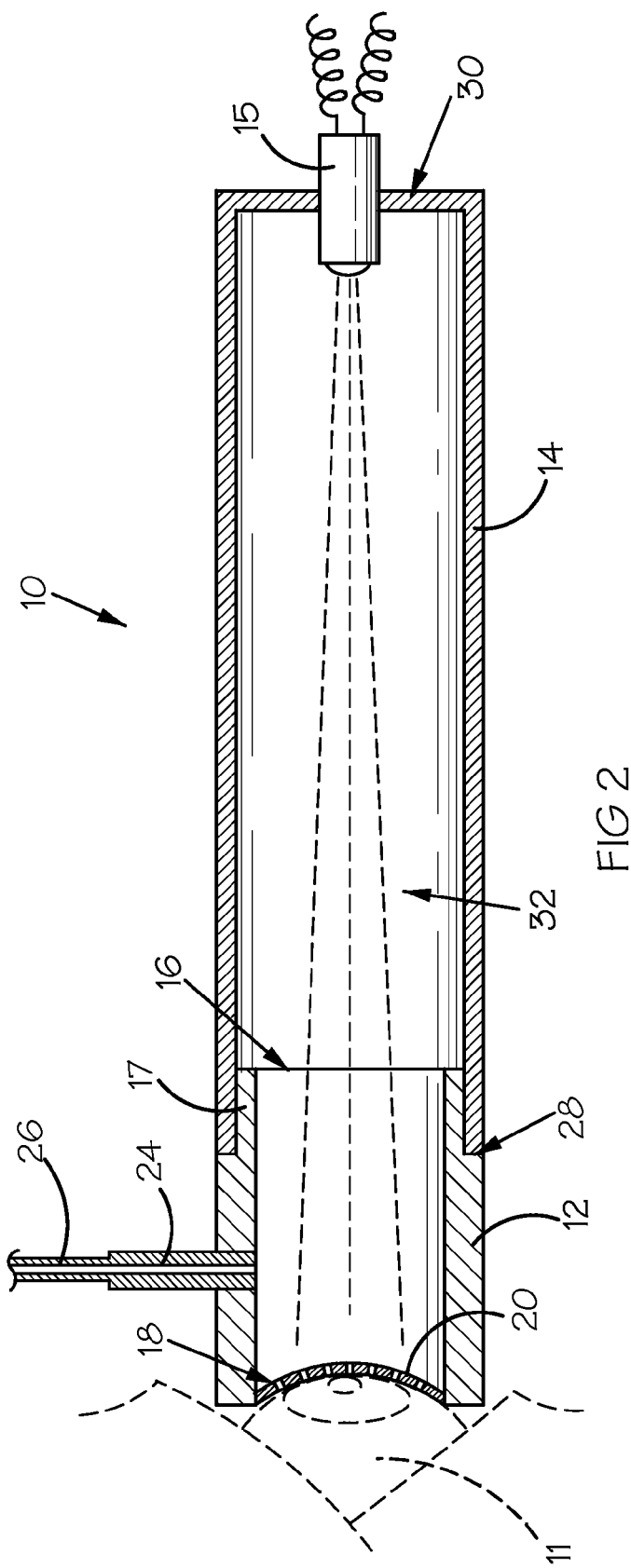
FIG. 2 shows a sectional side view of the device of FIG. 1.

With reference to the drawings, an ophthalmological device for the treatment of corneal diseases such as keratoconus and glaucoma, is designated generally by the reference numeral 10. The device 10 has a generally elongate cylindrical configuration and comprises a moulding head 12, a suction body 14 and a UV lamp 15.

The device 10 is specifically adapted for use in the treatment of corneal diseases wherein the moulding head 12 is used to shape the cornea of an eye of a patient while the UV lamp 15 is used to induce cross-linking of collagen fibres in the cornea by a photo-sensitizer such as riboflavin or a riboflavin solution.

The moulding head 12 is of a plastics material and has a generally hollow cylindrical configuration. The moulding head has a first end 16 which is open and a second end 18 in which a rigid glass moulding lens is mounted. The end 16 defines a boss 17. The moulding lens 20 defines a curved moulding surface 22 having a predetermined curvature. The lens 20 defines a plurality of apertures 21 therein, the purpose of which is explained hereinbelow. The moulding head 12 further includes a connector 24 to which a hose 26 which is connected to a suction pump, is connected.

The suction body 14 is aluminium and has a generally hollow cylindrical configuration and has a first end 28 and a second end 30. The first end 28 is open and is releasably fitted onto the boss 17 at the open end 16 of the moulding head in an airtight arrangement. The UV lamp 15 is fitted to the suction body 16 at its closed end 30 in an airtight manner. The UV lamp 15 is in the form of a light emitting diode (LED) which is operable to emit a beam of UV light having a wavelength of 375 nm. The aluminium of the suction body acts as a heat sink, cooling the suction body when it is heated by the LED, in use.

The moulding head 12 and the suction body 14 together define a chamber 32 from which air is evacuated as will be explained in further detail below, in order to induce a partial vacuum within the chamber 32.

In use, the device 10 is used in the treatment of corneal diseases, for example, keratoconus. In the treatment of keratoconus in accordance with the method of the invention, an effective amount of a photo-sensitizer such as riboflavin or a riboflavin solution is applied to an eye 11 of a patient. Thereafter a lens 20 of the moulding head 12 of the ophthalmological device 10 is pressed against the cornea so as to shape the cornea until a desired corneal shape is achieved. A suction is applied to the chamber defined by the moulding head 12 and the suction body 14 until a partial vacuum is created within the chamber 32 which causes a suction to be applied to the cornea of the eye so as to attract the cornea onto the moulding surface of the lens 20. The suction applied to the eye from within the chamber 32 enhances the moulding of the cornea by attracting the cornea onto the moulding lens while at the same time reducing intraocular pressure within the eye. While the cornea is held against the mould by the suction, the cornea is irradiated with a focussed beam of UV light by means of the UV lamp 15 thereby inducing a cross linking of the collagen fibres in the cornea of the eye which in turn increases the biomechanical rigidity of the cornea.

By being releasably secured to the suction body, the moulding head 12 can be removed and replaced with another moulding head having a lens which has a different curvature. In this manner, this allows the ophthalmological device 10 to be used with different moulding lenses for use with patient's having corneas having different curvatures. Furthermore, with the moulding head 12 removed, the ophthalmological device can be used for conventional cross-linking using a photo-sensitizer and beam of UV light only.

The method and device described hereinabove have been found to be useful as an adjunct in the treatment of certain types of glaucoma by lowering the intraocular pressure within the eye. The method and device described hereinabove have also been found to be useful in the treatment of keratoconus wherein the device is used to change the curvature of the cornea while simultaneously increasing the biomechanical rigidity of the cornea by inducing cross-linking of collagen fibres within the cornea.

The invention claimed is:

1. A non-surgical, non-heat based, ophthalmological device for the treatment of Keratonconus and Glaucoma, comprising:

a moulding head having a hollow, tubular body with an open first end and an open second end and a predetermined length, the second end being covered by a curved, transparent lens having a distal moulding surface, the lens having a plurality of apertures therein wherein the apertures are arranged coaxially in two circular rows including an inner row and an outer row, the moulding surface having a predetermined curvature, the moulding surface being adapted to be applied to the cornea of an eye of a patient for shaping the corneal tissue to the predetermined curvature, the transparent lens being adapted to transmit UV light;

a suction body having an elongated, hollow, tubular configuration with a first end and a second end, the first end of the suction body being connected to the first end of the body of the moulding head, the hollow interiors of the moulding head and the suction body defining a suction chamber in which a partial vacuum is adapted to be induced so as to form a partial vacuum within the moulding head which is adapted to attract the cornea onto the moulding surface through the lens apertures;

a UV lamp disposed at the second end of the suction body for directing a beam of UV light down the hollow interiors of the suction body and the moulding head through the transparent lens and to the cornea, whereby the UV lamp is spaced and separated from the moulding surface of the moulding head by the elongated suction body to reduce heating of the moulding surface;

a vacuum source communicatively connected to the moulding head for applying the partial vacuum within the hollow interiors of the suction body and moulding head to attract the cornea onto the moulding surface, the vacuum source being connected to the moulding head body a predetermined distance away from the moulding surface of the transparent lens via a suction connector disposed between the midpoint of the length and the second end;

whereby, in use, the cornea is being irradiated with UV light while it is being moulded into a predetermined shape by the vacuum acting on the transparent multi-apertured moulding surface;

whereby the partial vacuum provided by (1) the vacuum source connected away from the moulding surface a predetermined distance in the moulding head, (2) the suction chamber of the suction body, and (3) the plurality of apertures in the moulding surface of the moulding head provide an optimized moulding force to the patient's cornea during the non-heat based UV irradiation; and whereby the device does not use surgery, heat or a laser to mould the shape of the eye.

2. The ophthalmological device as claimed in claim 1, wherein the moulding head first end is removably connected to the first end of the suction body, thereby permitting the mould to be removed and replaced by another mould with a lens having at least a second predetermined curvature which is different than the predetermined curvature.

3. The ophthalmological device as claimed in claim 2, wherein the first end of the suction body the first end of the moulding head each have a boss type connecting formation that permit them to be removably connected.

4. The ophthalmological device as claimed in claim 1, wherein the UV lamp is an LED UV lamp, and wherein the UV LED lamp is operable to emit a beam of UV light having a wavelength of 375 nm.

5. The ophthalmological device as claimed in claim 1, wherein the inner row has eight apertures and wherein the outer row has seventeen apertures.

6. The ophthalmological device as claimed in claim 1, wherein the suction body is constructed of aluminium whereby it acts as a heat sink to insulate the moulding head from heat from the UV lamp during use to thereby minimize heating of the patient's cornea.

7. A method of treating Keratonconus and Glaucoma, comprising the steps of:
  applying an effective amount of a photo-sensitizer to a cornea of an eye of a patient;
  providing a non-surgical, non-heat based ophthalmological device comprising:
    (a) a suction body having an elongated, hollow, tubular configuration with a first end and a second end;
    (b) a UV lamp disposed at the second end of the suction body for directing a beam of UV light down the hollow interior of the suction body; and
    (c) a vacuum source communicatively connected to a moulding head for applying the partial vacuum within the hollow interior of the suction body;
  selecting a moulding head having a hollow, tubular configuration with a first end, a second end, and a predetermined length, the second end having a curved, transparent lens having a distal moulding surface, the transparent lens being adapted to transmit UV light, the lens having a plurality of apertures therein wherein the apertures are arranged coaxially in two circular rows including an inner row and an outer row, the moulding surface having a predetermined curvature, the moulding surface being adapted to be applied to the cornea of an eye of a patient for shaping the corneal tissue to the predetermined curvature, the first end of the moulding head being connected to the first end of the suction body, the hollow interiors of the moulding heads and the suction body defining a suction chamber in which a partial vacuum is adapted to be induced by the vacuum source so as to form a partial vacuum within the moulding head which is adapted to attract the cornea onto the moulding surface through the lens apertures;
  attaching the first end of the moulding head to the first end of the suction body, whereby the UV lamp is spaced and separated from the moulding surface of the moulding head by the elongated suction body to reduce heating of the moulding surface;
  applying the moulding head to the cornea thereby to shape the cornea until a desired corneal shape is achieved;
  applying a suction to the cornea, via the vacuum source through the hollow interiors of the suction body and the moulding head, and through the lens apertures, so as to attract the cornea onto the moulding surface of the mould, the vacuum source being connected to the moulding head body via a suction connector disposed between the midpoint of the length of the of the moulding head and the second end of the moulding head; and
  irradiating the cornea with a focused beam of UV light, transmitted down the hollow interiors of the suction body and the moulding head, through the lens, thereby to induce a cross-linking of collagen fibres in the cornea while the cornea is attracted onto the moulding surface of the moulding head by the vacuum acting on the transparent multi-apertured moulding surface;
  whereby the partial vacuum provided by (1) the vacuum source connected away from the moulding surface a predetermined distance in the moulding head, (2) the suction chamber of the suction body, and (3) the plurality of apertures in the moulding surface of the moulding head provide an optimized moulding force to the patient's cornea during the non-heat based UV irradiation; and
  whereby the method does not use surgery, heat or a laser to treat Keratonconus or Glaucoma.

* * * * *